United States Patent
Li et al.

(10) Patent No.: US 12,410,396 B2
(45) Date of Patent: Sep. 9, 2025

(54) RAPID CELL ISOLATION AND RECOVERY USING HOLLOW GLASS MICROSPHERES COATED WITH BIODEGRADABLE NANOSTRUCTURED FILMS

(71) Applicant: Texas Tech University System, Lubbock, TX (US)

(72) Inventors: Wei Li, Lubbock, TX (US); Ziye Dong, Lubbock, TX (US)

(73) Assignee: TEXAS TECH UNIVERSITY SYSTEM, Lubbock, TX (US)

(*) Notice: Subject to any disclaimer, the term of this patent is extended or adjusted under 35 U.S.C. 154(b) by 1040 days.

(21) Appl. No.: 17/285,884

(22) PCT Filed: Oct. 18, 2019

(86) PCT No.: PCT/IB2019/058916
§ 371 (c)(1),
(2) Date: Apr. 15, 2021

(87) PCT Pub. No.: WO2020/079665
PCT Pub. Date: Apr. 23, 2020

(65) Prior Publication Data
US 2021/0371813 A1    Dec. 2, 2021

Related U.S. Application Data

(60) Provisional application No. 62/747,487, filed on Oct. 18, 2018.

(51) Int. Cl.
*C12N 5/00* (2006.01)
(52) U.S. Cl.
CPC ........ *C12N 5/0075* (2013.01); *A61K 2236/53* (2013.01); *C12N 2531/00* (2013.01); *C12N 2533/12* (2013.01); *C12N 2533/30* (2013.01); *C12N 2533/50* (2013.01)

(58) Field of Classification Search
None
See application file for complete search history.

(56) References Cited

PUBLICATIONS

PCT/IB2019/058916. International Search Report & Written Opinion (Jan. 23, 2020).
Dong et al. "Enhanced capture and release of circulating tumor cells using hollow glass microspheres with a hanostructured surface." Nanoscale, Issue 35 (2018).
Dong et al. "Cell isolation and recovery using hollow glass microspheres coated with nanolayered films for applications in resource-limited settings." ACS Appl. Mater. Interfaces 2017 9, 18, 15265-15273 (Apr. 17, 2017).

*Primary Examiner* — Nora M Rooney
(74) *Attorney, Agent, or Firm* — LOZA & LOZA, LLP; Kevin L. Soules (57) ABSTRACT

Hollow glass microspheres (HGMS) with a controlled nano-topographical surface structure ($^{NS}$HGMS) demonstrate improved isolation and recovery of cell from biological fluid. $^{NS}$HGMS can be achieved by applying layer-by-layer (LbL) assembly of negatively charged SiO2 nanoparticles and positively charged poly-L-arginine molecules. Then, a sheathing can be applied to the surface with an enzymatically degradable LbL film made from biotinylated alginate and poly-L-arginine. Further, a cap of anti-EpCAM antibodies and anti-fouling PEG molecules can be applied to the sheathed film covering the microspheres. Compared to smooth-surfaced HGMS, NSHGMS reveals shorter isolation times, enhanced capture efficiency and lower detection limit in, for example, commonly used cancer cell lines. An $^{NS}$HGMS-based cell isolation method does not require specialized lab equipment or an external power source, and thus, can be used for separation of targeted cells from blood or other body fluid in a resource-limited environment.

7 Claims, 7 Drawing Sheets

100

110 — APPLY NEGATIVELY CHARGED SiO₂ NANPARTICLES AND POSITIVELY CHARGED POLY-L-ARGININE MOLECULES TO MICROSPHERES

120 — SHEATH THE SURFACE OF NEGATIVELY CHARGED SiO₂ NANOPARTICLES AND POSITIVELY CHARGED POLY-L-ARGININE MOLECULES COVERING THE MICROSPHERES WITH AN ENZYMATICALLY DEGRADABLE LBL FILM MADE FROM BIOTINYLATED ALGINATE AND POLY-L-ARGININE CAN BE ACCOMPLISHED

130 — CAP SHEATHED FILM WITH ANTI-EPCAM ANTIBODIES AND ANTI-FOULING PEG MOLECULES

RAPID CELL ISOLATION AND RECOVERY USING HOLLOW GLASS MICROSPHERES COATED WITH BIODEGRADABLE NANOSTRUCTURED FILMS

PRIORITY

The present embodiments claim priority as a continuation of U.S. Provisional Patent Application 62/747,487, filed Oct. 18, 2018, entitled "RAPID CELL ISOLATION AND RECOVERY USING HOLLOW GLASS MICROSPHERES COATED WITH BIODEGRADABLE NANOSTRUCTURED FILMS", which is herein incorporated by reference.

TECHNICAL FIELD

The present embodiments are generally related to cell isolation techniques. More particularly, embodiments are related to the application and use of topographical surface to hollow glass microspheres to enhance the likelihood of capturing cells in fluid using the hollow glass microspheres.

BACKGROUND

Established cell isolation and purification techniques such as fluorescence activated cell sorting (FACS), isolation through magnetic micro/nano-particles, and recovery via microfluidic devices have limited application as disposable technologies appropriate for point-of-care use in remote areas where lab equipment as well as electrical, magnetic, and optical sources are restricted. Most of these approaches involve sophisticated microfabrication, excessive lab equipment, long process times and are labor intensive, which limit their practical usage in resource-limited settings.

To develop and employ a reliable method of cell isolation in a resource-limited condition, the following issues need to be addressed. First, the isolated cells should have high viability. Second, the phenotype of the cells should be well preserved for downstream studies. Cells should not be exposed to stresses that are known to affect cell phenotype, including high shear forces, harmful reagents, and non-physiological temperatures and pH levels. Further, any employed method should achieve both high efficiency of cell recovery and cell purity. Non-specific retention of untargeted cells needs to be diminished. Finally, the approach should be feasible for disposable point-of-care use even in remote areas with minimal access to sophisticated lab equipment and complex electrical, magnetic, or optical sources.

Microspheres (also referred to as "microbubbles") covered with cell specific antibodies have been used for the isolation of specific cells or other biologic particles within a fluid (e.g., blood). The smooth surface of microspheres, however, reduces their capture effectiveness. What is needed is a way to increase the effective of capturing cells or other biologic particles in fluid using microspheres.

The present inventors introduce a process and materials that can create a topographical surface on the microspheres and thereby alter the smooth surface of the microspheres in order to significantly increase capture effectiveness especially where concentrations of cells in a sample may be very low. Self-floating hollow glass microspheres with a nanostructured surface can isolate and recover circulating tumor cells in blood (and other cells in other body fluids) with shorter processing time, enhanced capture efficiency and lower detection limit.

SUMMARY OF EMBODIMENTS

In accordance with a feature of the embodiments, a topographical structure is added to the surface of a bead representing the microsphere to create a non-smooth surface using a nanostructure ($^{NS}$HGMS). The introduction of the topographical structures allows for an increased surface area that will allow for more antibodies to come in contact with the desired cells.

It is a feature to provide a method for providing rapid cell isolation and recovery that includes providing hollow glass microspheres coated with a biodegradable nanostructured film within a fluid, and then using coated microspheres for the isolation and recovery of cells on the nanostructured film from fluid using the microspheres, in accordance with the embodiments.

It is a features to provide glass microspheres with an added topographical structure to make the surface of the microspheres non-smooth. This can be accomplished using a nanostructure (nsHGMS). The introduction of the topographical structures allows for an increased surface area that will allow for more antibodies to come in contact with the desired cells.

It is also a features to provide hollow glass microspheres with surface cracks and/or surface imperfection to increase the surface area of the microspheres, thus improving the number of binding sites and binding affinity.

It is another feature to provide hollow glass microspheres coated with a biodegradable nanostructured film for use in the isolation and recovery of cells in fluid, wherein the nanostructured film further comprises negatively charged $SiO_2$ nanoparticles and positively charged poly-L-arginine molecules applied to a surface of the hollow glass microspheres, in accordance with the embodiments.

It is another feature to provide hollow glass microspheres coated with a biodegradable nanostructured film for use in the isolation and recovery of cells in fluid, wherein the negatively charged $SiO_2$ nanoparticles and positively charged poly-L-arginine molecules are applied to the surface of the hollow glass microspheres using layer-by-layer disposition, in accordance with the embodiments.

It is yet another feature to provide hollow glass microspheres coated with a biodegradable nanostructured film for use in the isolation and recovery of cells in fluid, wherein the surface of the hollow glass microspheres including the negatively charged $SiO_2$ nanoparticles and positively charged poly-L-arginine molecules is then sheathed with an enzymatically degradable LbL film made from biotinylated alginate and poly-L-arginine, in accordance with the embodiments.

It is a feature to provide microspheres coated with biodegradable nanostructured film for use in the isolation and recovery of cells in fluid, wherein negatively charged $SiO_2$ nanoparticles, positively charged poly-L-arginine molecules, and enzymatically degradable LbL film made from biotinylated alginate and poly-L-arginine are applied to the surface of the hollow glass microspheres using layer-by-layer disposition, in accordance with the embodiments.

It is another feature to provide hollow glass microspheres coated with a biodegradable nanostructured film for use in the isolation and recovery of cells in fluid, wherein negatively charged $SiO_2$ nanoparticles and positively charged poly-L-arginine molecules covering microspheres are sheathed with an enzymatically degradable LbL film made from biotinylated alginate and poly-L-arginine and then are capped with anti-EpCAM antibodies and anti-fouling PEG molecules, in accordance with the embodiments.

It is another feature to provide hollow glass microspheres coated with a biodegradable nanostructured film for use in the isolation and recovery of cells in fluid, wherein negatively charged $SiO_2$ nanoparticles, positively charged poly-L-arginine molecules, enzymatically degradable LbL film made from biotinylated alginate and poly-L-arginine, and a cap of anti-EpCAM antibodies and anti-fouling PEG molecules are each applied to the surface of the hollow glass microspheres using layer-by-layer disposition, in accordance with the embodiments.

It is also a feature to provide hollow glass microspheres coated with a biodegradable nanostructured film for use in the isolation and recovery of cells in fluid that are effective for rapid cell isolation and recovery using layer-by-layer (LbL) application of negatively charged $SiO_2$ nanoparticles and positively charged poly-L-arginine molecules to a surface of hollow glass microspheres, in accordance with the embodiments.

It s a feature to provide a cell isolation and recovery microstructure system including microspheres coated with a biodegradable nanostructure film applied the to microspheres via layer-by-layer disposition, wherein the microstructure system isolates and recovers cells in accordance with the embodiments, in accordance with the embodiments, in accordance with the embodiments.

It s a feature to provide a cell isolation and recovery microstructure system including microspheres coated with a biodegradable nanostructure film applied the to microspheres via layer-by-layer disposition, wherein the biodegradable nanostructure film further comprises negatively charged $SiO_2$ nanoparticles and positively charged poly-L-arginine molecules applied to a surface of the hollow glass microspheres, in accordance with the embodiments.

It s a feature to provide a cell isolation and recovery microstructure system including microspheres coated with a biodegradable nanostructure film applied the to microspheres via layer-by-layer disposition, wherein the surface of the hollow glass microspheres including the negatively charged $SiO_2$ nanoparticles and positively charged poly-L-arginine molecules can include a sheathing of enzymatically degradable LbL film made from biotinylated alginate and poly-L-arginine, in accordance with the embodiments.

It is a feature to provide a cell isolation and recovery microstructure system including microspheres coated with a biodegradable nanostructure film applied the to microspheres via layer-by-layer disposition, wherein the surface of the hollow glass microspheres including the negatively charged $SiO_2$ nanoparticles and positively charged poly-L-arginine molecules sheathed with enzymatically degradable LbL film made from biotinylated alginate and poly-L-arginine further comprises a cap of anti-EpCAM antibodies and anti-fouling PEG molecules, in accordance with the embodiments.

DETAILED DESCRIPTION

The disclosed technology relates tangentially to the Biomedical Research Industry. Biomedical research encompasses all research that is done to further the field of science. Cell isolation used in almost every lab to conduct in vitro studies. The disclosed technology has the potential to be used as a cheap and effective cell sorting method. The disclosed technology also has value in the in vitro diagnostics market. The disclosed technology will offer a simple and cheap method testing patients' blood for certain cells that could be markets for cancer and other diseases.

Personalized medicine requires isolation of targeted cells with high purity, high viability and high specificity. Easy processing and minimal sample preparation are also preferred in this field. The disclosed embodiments can be utilized in a surgical room to achieve fast isolation of targeted cells for downstream molecule analysis and the development of personalized disease model. The embodiments can also be applied to the isolation of T-cells for immunotherapy.

Microspheres or microbubbles are buoyant and can be used to achieve cell isolation in fluid. Adding $SiO_2$ nanoparticles to the surface of microspheres can produce a topographical or rough surface on the microspheres. This application allows for an increased surface area on the microspheres that contains antibodies and can create valleys or crevasses in the sphere surface that can allow for multiple antibodies to potentially grab onto the targeted cells. This improvement allows for a significantly more effective method of cell isolation. Glass microspheres with an added topographical structure make the surface of the microspheres non-smooth. This can be accomplished using a nanostructure (nsHGMS). The introduction of the topographical structures allows for an increased surface area that will allow for more antibodies to come in contact with the desired cells. It can also be a feature to provide hollow glass microspheres with surface cracks and/or surface imperfection to increase the surface area of the microspheres, thus improving the number of binding sites and binding affinity.

Disclosed are methods, structures and systems for achieving cell (including bacterial) isolation that requires neither specialized lab equipment nor any form of external power source. The present inventors have utilized self-floating hollow glass microspheres (HGMSs) coated with an enzymatic degradable thin film and conjugated with antibodies to allow both fast capture and release of subpopulations of cells from a large cell mixture. Cell capture is mediated by the interactions between antibodies on the surface of HGMSs and surface markers on the targeted cells. Captured cells automatically float to the top of the hosting liquid and separate from the untargeted cells. For isolation of bacteria, which are typically much smaller than cells, bacteria targeting nanoparticles are introduced into the cell mixture first, followed by the addition of nanoparticle-targeting hollow glass microspheres; the subsequent capture interaction is similar to the cell capture explained above. The cells are then recovered by degrading the link between the cells and the HGMSs.

As an example application and need for the embodiments disclosed herein, circulating tumor cells (CTCs), derived from primary tumor sites, can travel through the bloodstream to distant organs, causing metastasis and cancer-related death. Therefore, isolation and analysis of CTCs in peripheral blood, (liquid biopsy), has attracted attention because it can be used for cancer prognosis and allow personalized treatment for cancer patients. However, it is still a challenge to capture CTCs effectively with high purity due to their rare number (1-100 in $10^9$ blood cells). By taking advantage of specific cancer cell surface markers, such as the epithelial cell adhesion molecule (EpCAM), CTCs can be isolated by maximizing the adhesion of CTCs with antibody-modified surface.

Microfluidic devices are widely used for CTC isolation, owing to the precise fluidic manipulation coupled with high surface-to-volume ratio. Generally, blood samples continuously flow at a relatively low flow rate through microfluidic devices; there, antibodies modified on channel surface can collect CTCs and blood cells are allowed to pass. As an alternative to microfluidic devices, immunomicro/nano-bead-based CTC isolation methods are relatively simple for both production and application. For example, CellSearch™ is the first and only FDA approved product for CTC application, where CTCs are attached with antibody-conjugated nanomagnetic particles, and separated by a magnetic field. However, this approach requires large quantity of magnetic nanoparticles in cell isolation, which could compromise the purity of enriched cells. Further, viability of the isolated CTCs drops due to internalization of magnetic nanoparticles. Although larger microparticles could be used to enhance cell viability, it was found that beads with sizes larger than six microns are less effective in capturing cancer cells due to the beads lower surface area.

Recent studies indicate that nanotopography of the substrates underneath the antibody molecules demonstrates significant effect on CTC adhesion. Microchips with inner surfaces modified with nanostructures (such as nanopillars, nanodots, nanofibers, and nanofractals) showed enhanced capture performance. Recently, self-floating hollow glass microspheres (HGMS) modified with tumor-specific antibodies have been developed in the present inventors lab for capture of CTCs in resource-limited settings; these HGMSs demonstrated effective cell isolation and good viability of isolated cancer cells when the concentration of spiked cells is larger than several thousand per milliliter. Capture efficiency, however, dramatically decreases if the spiked cell concentration in blood is below 1000 cells/mL, probably due to insufficient interactions between cancer cells and the HGMS surface. In order to apply the HGMS approach for CTC isolation to clinically relevant samples with concentrations from a few to several hundred cells/mL, the present inventors determined that it would be more desirable to create nanostructures on the HGMS surface and enhance cell-surface interactions. Nonetheless, current microfabrication methods for generating nanostructured-surface (i.e., chemical etching, chemical vapor deposition, electrochemical deposition, or electrospinning) are not feasible for surface coating of microparticles.

Self-floating hollow glass microspheres (HGMS) modified with tumor-specific antibodies have been developed by the present inventors for capture of circulating tumor cells (CTCs), and have demonstrated effective cell isolation and good viability of isolated cancer cells. The present inventors have discovered that the capture efficiency, however, can decrease dramatically if the spiked cell concentration is low, possibly due to insufficient interactions between cells and the HGMS' surface. In order to apply an HGMS-based, CTC isolation to clinically relevant samples, the present inventors have determined that it is desirable to create nanostructures on the surface of HGMS to enhance cell-surface interactions. Current microfabrication methods, however, cannot generate nanostructured-surface on the microspheres.

Because of the shortcomings of microfabrication capabilities, the present inventors have developed a new HGMS with controlled nanotopographical surface structure (herein referred to as "NsHGMS"), and have demonstrated isolation and recovery of rare cancer cells utilizing the new HGMS with controlled nanotopographical surface structure. Using cancer cells as an example, $^{NS}$HGMS reveal shorter isolation time (20 min.), enhanced capture efficiency (93.6±4.9%) and lower detection limit (30 cells/mL) for commonly used cancer cell lines (MCF7, SK-BR-3, PC-3, A549 and CCRF-CEM) when compared to smooth-surfaced HGMS. As a further benefit, this $^{NS}$HGMS-based CTC isolation method does not require specialized lab equipment or an external power source, and thus, can be used for separation of targeted cells from blood or other body fluid in a resource-limited environment.

Layer-by-layer (LbL) assembly is a versatile technique for surface modification and not limited by the shape of substrates (planar and particulate substrates) or materials for deposition (polymers, proteins, lipids, nucleic acids, and nanoparticles). Generally, electrostatic interaction is the most common driving force for LbL assembly, where positively and negatively charged macromolecules are adsorbed onto substrates alternatively, allowing the incorporation of electronically charged species. Metal and polymer nanoparticles can also be used as building blocks and successfully embedded in the LbL films for applications in drug delivery, optical devices, and batteries.

$^{NS}$HGMS was achieved by applying layer-by-layer (LbL) assembly of negatively charged $SiO_2$ nanoparticles (NPs) and positively charged poly-L-arginine molecules. The surface was then sheathed with an enzymatically degradable LbL film made from biotinylated alginate and poly-L-arginine, and then capped with anti-EpCAM antibodies and anti-fouling molecules. Compared to HGMS with smooth surface, $^{NS}$HGMS showed shorter isolation time (20 min.), enhanced capture efficiency (93.6±4.9%) and lower detection limit (30 cells/mL) for many cancer cell lines (MCF7, SK-BR-3, PC3, A549, CCRF-CEM). The $^{NS}$HGMS-based CTC isolation method does not require specialized lab equipment or an external power source, making it possible to rapidly perform separation of targeted cells from blood or other body fluids in a surgical room or other resource-limited environments.

Figure 1:
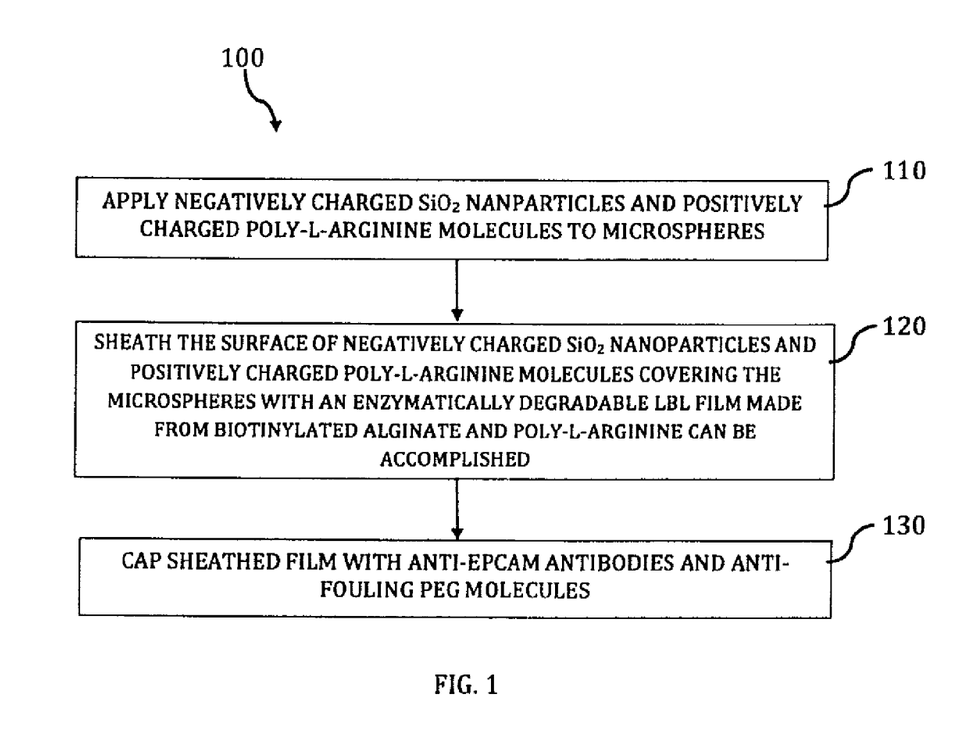
Referring to FIG. 1, a flow diagram of a process is illustrated, in accordance with the embodiments.

Referring to FIG. 1, $^{NS}$HGMS can be achieved by applying layer-by-layer (LbL) assembly of negatively charged SiO2 nanoparticles and positively charged poly-L-arginine molecules to microspheres as shown in Step 110. Then as shown in Step 120, sheathing the surface of negatively charged SiO2 nanoparticles and positively charged poly-L-arginine molecules covering the microspheres with an enzymatically degradable LbL film made from biotinylated alginate and poly-L-arginine can be accomplished. Then, as shown in Step 130, the resulting film as sheathed can be capped with anti-EpCAM antibodies and anti-fouling PEG molecules.

During an experiment, Alginate (ALG) (Pronova UPMVG, 60% guluronate, 40% mannuronate, Mw=120,000) were acquired from Novamatrix, Norway. Poly-L-arginine (PARG, $M_w$=15,000-70,000) was acquired from Sigma-Aldrich and used without further purification. Poly (ethylene glycol) 2-aminoethyl ether biotin (NH2-PEG-biotin, Mw=20,000)(PEG20 000) was acquired from Nanocs Inc. Neutravidin (Mw=60,000), NeutrAvidin-Texas Red conjugate (A-2665), 1-ethyl-3-(-3-dimethylaminopropyl) carbodiimide hydrochloride (EDC), and N-hydroxysulfosuccinimide (Sulfo-NHS) were acquired from ThermoFisher Scientific. Biotin conjugated EpCAM (CD326) monoclonal antibody was provided by Fisher Scientific. Biotin conjugated mouse antihuman CD71 was obtained from BD Bioscience. Alginate Lyase (A1603) was acquired from Sigma Aldrich. Blood from health donors was purchased from BioreclamationIVT (Westbury, NY) and used within 3 days of collection. Hollow glass microspheres (HGMS, density=0.47 g/mL and diameter range of 20-27 μm) were obtained from Cospheric LLC. Silica nanoparticles (SiO$_2$ NPs) (with nm size of 20, 40, 80, 120, and 200) were acquired from General Engineering & Research. All other reagents were acquired from Sigma Aldrich, USA, and used as received.

Alginate was modified with biotin hydrazide (Sigma B7639) using standard EDC reaction as reported in previous works. Briefly, 2-ethanesulfonic acid (MES) buffer (pH=6.1) was used to prepare 1.0 wt % of ALG solution. Then 0.16 wt. % biotin hydrazide, 0.72 wt. % EDC, and 0.41 wt. % Sulfo-NHS were added to the ALG solution and reacted for 3 hours. Then the solution was dialyzed against deionized H$_2$O for 48 hours and lyophilized to recover biotin modified alginate (BALG).

PARG and BALG were dissolved in deionized water (DI water) at a concentration of 2 mg/mL. SiO$_2$ NPs were dispersed in DI water to prepare a 10 wt. % suspension. The LbL deposition process involves the repeated sequential incubation of HGMS into aqueous solutions of positively and negatively charged materials, with a washing step in between. PARG and SiO$_2$ NP solutions were first used to modify HGMS surface. After two cycles of deposition, PARG and BALG solutions were used to form two bilayers of LbL film.

LbL film assembly was examined by a quartz-crystal microbalance with dissipation monitoring (QCM-D) (Q-Sense, E4 model, Sweden) and recorded at different overtones (n=3th, 5th, 7th, 9th, 11th and 13th). SiO$_2$ QCM-D (Q-sense, QSX 303) crystals were used as substrates and cleaned by a plasma cleaner for 5 minutes before experiment. To monitor LbL film adsorption process, PARG and SiO2 NP solutions were introduced into the QCM-D flow cell for 5 min with 5 min rinse steps in between. After two repeats of deposition, PARG and BALG solutions were pumped in the QCM-D flow cell to perform another two cycles of adsorption according to the previous protocol. The flow rate for all liquids was 0.15 mL/min.

The QCM-D results were analyzed with QTools (version: 3.1.30.624) to estimate adsorption mass based on the Voigt-based model as following:

$$\Delta F \approx -\frac{1}{2\pi\rho_0 h_0}\left\{\frac{\eta_3}{\delta_3} + \sum_{j=k}\left[h_j\rho_j\omega - 2h_j\left(\frac{\eta_3}{\delta_3}\right)^2\frac{\eta_j\omega^2}{\mu_j^2+\omega^2\eta_j^2}\right]\right\}$$

$$\Delta D \approx \frac{1}{2\pi f\rho_0 h_0}\left\{\frac{\eta_3}{\delta_3} + \sum_{j=k}\left[2h_j\left(\frac{\eta_3}{\delta_3}\right)^2\frac{\eta_j\omega}{\mu_j^2+\omega^2\eta_j^2}\right]\right\}$$

where, for a total of k viscoelastic layers under a bulk Newtonian fluid, $\rho_0$ and $h_0$ are the density and thickness of the quartz crystal, $\eta_3$ is the viscosity of the bulk fluid, δ3 is the viscous penetration depth of the shear wave in the bulk fluid, $\rho_3$ is the density of liquid, μ is the elastic shear modulus of an overall layer, and ω is the angular frequency of the oscillation. 0.0088 Pa·s was assumed as liquid viscosity. 1010 kg·m$^{-3}$, 1050 kg·m$^{-3}$ and 2650 kg·m$^{-3}$ were used to estimate liquid, polymer film and SiO$_2$ densities. Calculation used six overtones: 3th, 5th, 7th, 9th, 11th and 13th.

A human breast cancer cell line, MCF7 (ATCC HTB-22), was cultured at 37° C. in DMEM medium containing 10% fetal bovine serum (FBS) and 1% penicillin/streptomycin. A human breast cancer cell line, SK-BR-3 (ATCC HTB-30), was cultured at 37° C. in RPMI-1640 medium containing 10% fetal bovine serum (FBS) and 1% penicillin/streptomycin. A human prostate cancer cell line, PC-3 (ATCC CRL-1453), and a human lung cancer cell line, A549 (ATCC CCL-185), were cultured at 37° C. in F-12K growth medium containing 10% FBS and 1% penicillin/streptomycin. A human T lymphoblast cell line, CCRF-CEM (ATCC CRM-CCL-119), was cultured in RPMI-1640 medium with 10% fetal bovine serum (FBS) and 1% penicillin/streptomycin. Adhesion cells were released from culture flasks through incubation in 0.25% trypsin-EDTA (Invitrogen, CA) at room temperature for 5 min. Prior to spiking into blood, all cells were labeled with a fluorescent cellular dye (CellTracker™ Deep Red or CellTracker™ Blue, ThermoFisher) following the manufacturers' protocol. The cell suspension was subsequently constructed to the desired concentration in 5× diluted blood. Concentration of cancer cells in the suspension ranged from 30 cells/mL to 1,000 cells/mL.

After modifying the surface with SiO$_2$ NPs and PARG/BALG film, the coated HGMS were incubated with a Neutravidin solution (0.05 mg/mL) for 1 h. After washing by PBS, a mixture solution (20 μg/mL biotinylated anti-EpCAM and 20 μg/mL NH2-PEG-Biotin) was employed to coat EpCAM antibody and PEG molecules on the surface of Neutravidin functionalized NsHGMS.

For cell isolation, the $^{NS}$HGMS and cancer cells spiked diluted blood were mixed on a rotator at 10 rpm for 60 min at room temperature. After incubation, the HGMS were carefully harvested and incubated with 100 μL ACK lysing buffer (ThermoFisher Scientific A1049201) in a polydimethylsiloxane (PDMS) micro-well. The uncaptured blood was transferred into a 96-well plate where red blood cells were lysed by adding 200 µL ACK lysing buffer to each well. The numbers of depleted and captured cancer cells were quantified using an optical microscope (Olympus BX53). To release captured cancer cells, the top layer of PARG/BALG film was degraded by adding alginate lyase (100 µL at 1 mg/mL) for 10 minutes. Capture efficiency and captured cells purity are defined as follows:

$$\text{Capture efficiency} = \frac{\text{Number of captured cancer cells}}{\text{Total number of spiked cancer cells}}$$

Purity of captured cells =

$$\frac{\text{Number of captured cancer cells}}{\text{Total number of captured cancer cells and blood cells}}$$

Fluorescent images were taken with an EVOS FL microscope (Life Technologies). DAPI, GFP, Texas Red and Deep Red images were taken at nm wavelengths of 345, 488, 530, and 630, respectively.

The viability of recovered cancer cells was evaluated with a standard Live/Dead fluorescent assay (Life Technologies L3224) using manufacture's standard protocol and compared with control cells that had not been processed with $^{NS}$HGMS.

Hollow glass microspheres were characterized by scanning electron microscopy (SEM, Hitachi S-4300, Japan) at 5 kV. Cells were fixed by 2% glutaraldehyde in PBS solution for 12 h. $^{NS}$HGMS were washed by DI water. All samples were gradually rinsed with 20%, 40%, 60%, 80% and 100% ethanol, and dried at room temperature for 12 hours. The dried samples were gold-coated by a sputter and scanned under SEM at 300×, 1000×, 2500× and 50000× magnifications.

Data analysis was performed between groups using one-way ANOVA (n=3) by software Graphpad Prism 6.0. Calculated probabilities of $p<0.0001$, $0.0001<p<0.001$, $0.001<p<0.01$, $0.01<p<0.05$ and $p>0.05$ were represented by **, *, **, * and N.S., respectively.

HGMS with smooth surfaces have been developed for capture CTCs and have demonstrated effective cell isolation and good viability of isolated cancer cells. However, CTC capture was not efficient when the spiked cell concentration in blood is below several thousand per milliliter of blood, possibly due to insufficient interactions between cancer cells and HGMS' surface. In order to improve performance for CTC isolation for clinical patient samples (normally in the range of a few to several hundred cells per mL), a potential strategy is to enhance cell-surface interaction by creating nanotopographical structures on the HGMS' surface. The LbL deposition process was used to construct both nanostructures and biodegradable coating on the surface of HGMS. To build nanostructures on HGMS, SiO2 NPs were chosen because they are chemically inert, physically robust and intrinsically negatively charged. To compensate the charge, poly-L-arginine (PARG) was selected as the positively charged building block; this was used in previous work and showed good biocompatibility. Taking advantage of the flexibility of charged materials that are introduced during each deposition, alginate (ALG) was selected as another negatively charged component to form a layer of nanofilm coating on the $SiO_2$ nanostructures. ALG can easily conjugate with biotin molecules for further modification of the surface with antibodies to capture cancer cells. Further, PARG/ALG film can be rapidly enzymatically degraded in a mild condition, which provides a noninvasive way to quickly release capture cells and preserve high cell viability.

Figure 2:
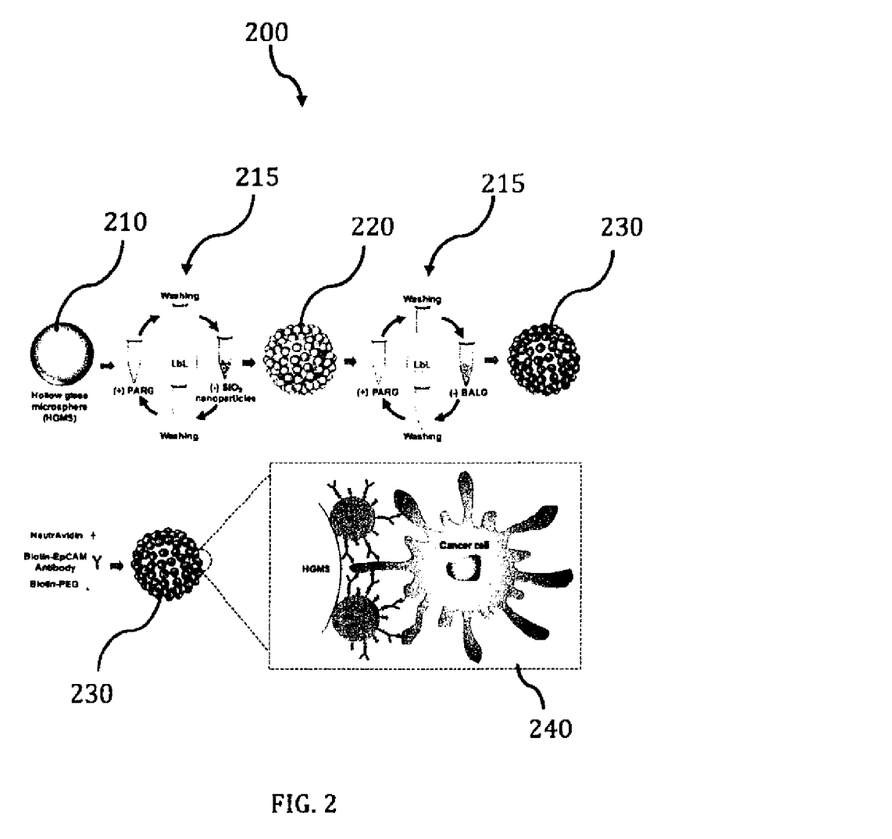
Referring to FIG. 2, material and fabrication process of hollow glass microspheres with nanotopographical structures ($^{NS}$HGMS) is illustrated, in accordance with the embodiments.

The detailed fabrication process of $^{NS}$HGMS 200 is shown in FIG. 2. A HGMS 210 can be first incubated with PARG and $SiO_2$ NP solutions alternatively to form nanotopographical structures on the surface of HGMS, as shown in step 210. Then, these HGMS coated with PARG and SiO2 220 can be coated with PARG and BALG as shown in step 215 to provide degradable coating and biotin molecules 230 for further functionalization. Next, the $^{NS}$HGMS were conjugated with anti-EpCAM antibody and PEG molecules via biotin-avidin interaction as shown in step 230. Finally, the $^{NS}$HGMS are ready for cancer cell capture as shown by blown up surface details in box 240.

Figure 3:
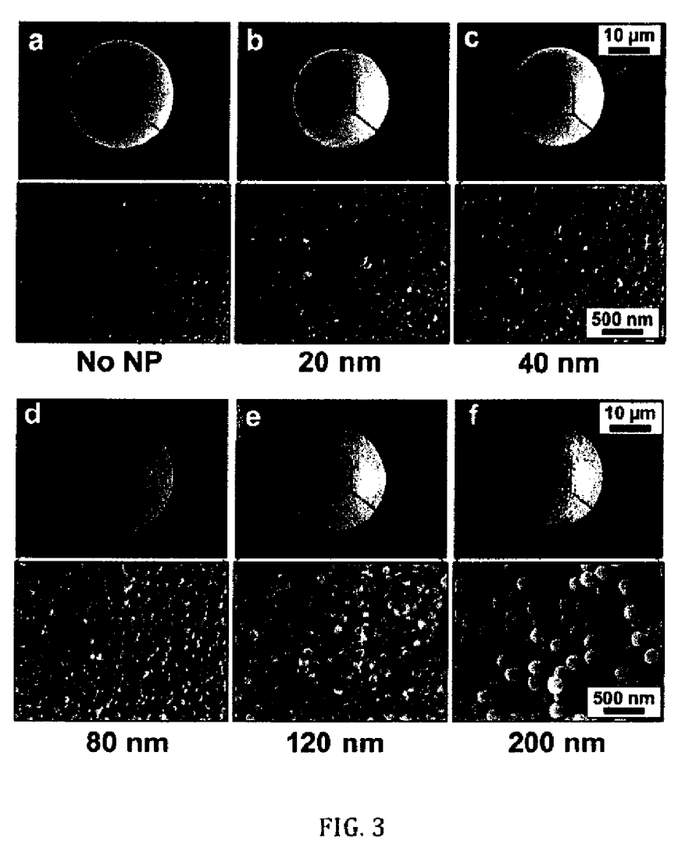
Referring to FIG. 3, illustrated are SEM images of $^{NS}$HGMS with zero to 200 nm of $SiO_2$, in accordance with the embodiments.

To illustrate the versatility of this method, five kinds of $SiO_2$ NPs with different diameters (20 nm, 40 nm, 80 nm, 120 nm, and 200 nm) were used to conduct the LbL deposition process. The resulting $^{NS}$HGMS were examined by SEM as shown in FIG. 3. The surface of HGMS was covered by $SiO_2$ NPs with various sizes using layer-by-layer (LbL) assembly process as follows: (a) no $SiO_2$, (b) 20 nm, (c) 40 nm, (d) 80 nm, (e) 120 nm and (f) 200 nm. The scale bar is 10 µm in the first and third rows, and 500 nm in the second and forth rows The HGMS modified only with PARG/BALG polymers showed smooth surfaces, while $SiO_2$ NP-modified $^{NS}$HGMS presented rough surfaces. The enlarged views (2nd and 4th rows) clearly display the nanotopographical structures of deposited $SiO_2$ NPs. After two cycles of deposition, the surfaces of $^{NS}$HGMS were uniformly covered by $SiO_2$ NPs. The nanoscale bumps and valleys formed on the surface of $^{NS}$HGMS could facilitate the contact between the surface components of the targeted cancer cells and HGMS surfaces and provide more interaction sites for cell-HGMS bonding.

Figure 4:
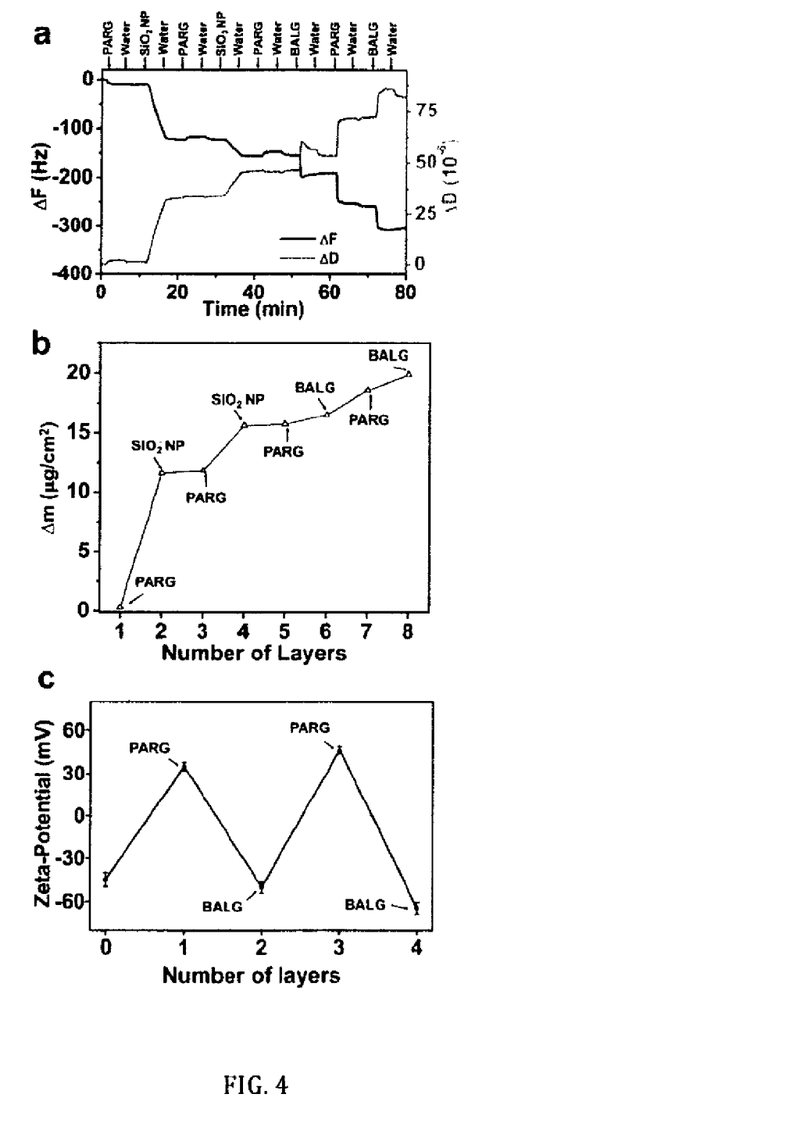
Referring to FIG. 4, graphical representing for monitoring of the LbL deposition process of $^{NS}$HGMS are illustrated, in accordance with the embodiments.

To best understand the LbL assembly process for creating nanotopographical structure on the surface of HGMS, QCM-D was used to monitor each of the material adsorption steps. In this experiment, a sensor placed in a QCM-D flow cell was put in contact with solutions in the same order as the LbL process for $^{NS}$HGMS. As illustrated in FIG. 4, in QCM-D, the change of resonance frequency (F) represents the mass of adsorbed or bound materials while dissipation (D) indicates the viscoelastic stiffness of the attached molecules. The decreasing of F values suggests adsorption of molecules on the surface, while the increasing of D values implies attachment of softer molecules.

FIG. 4a illustrates a stepwise decrease of F value for the QCM sensor in the process of LbL assembly, indicating successful adsorption of designated material on the surface of the sensor. FIG. 4b shows the mass of the absorbed materials during each step, calculated using the change of F values from FIG. 4a. During the two adsorption steps of $SiO_2$ NPs (200 nm), mass additions of 13.3 µg/cm2 and 3.8 µg/cm$^2$ were observed, which corresponded to $1.02*10^9$ cm-2 and $3.43*10^8$ cm$^{-2}$ surface coverage of $SiO_2$ NPs, respectively. A total density of $SiO_2$ NPs covered on the surface of the QCM sensor was approximately $1.363*10^9$ particles per cm$^2$. Considering the desorption of $SiO_2$ NPs off the surface of QCM sensor due to the constant shear stress applied on, this value maybe lower than the real coverage of $SiO_2$ NPs on the surface of NSHGMS. After deposition of SiO2 NPs, adsorption of PARG and BALG molecules was repeated two times to form a thin multifunctional LbL film on the outmost surface of $^{NS}$HGMS, which allows conjugation of antibody for cancer cell capture and biodegradation for cancer cell release. From the resonance frequency change shown in FIG. 4a, the mass of this [PARG/BALG]$_2$ film was approximately 4.2 µg/cm$^2$. Successful coating of the PARG/BALG film was also confirmed from alternation of surface zeta potential after adsorption oppositely-charged polymers, as shown in FIG. 4c. The values on the zeta-potential during LbL deposition were in good agreement with those from previous reported work. It is noted that the outmost surface was capped by BALG molecules.

To ensure noninvasive release of captured cancer cells and to preserve the viability of released cells, it is essential that the outmost antibody-embedded film quickly degrades under mild conditions. Also required is that the SiO$_2$ NPs beneath the PARG/BALG film should not peel off from the HGMS surface. Undesired peeling of SiO$_2$ NPs may be taken up by the cancer cells and cause cell apoptosis. Fluorescence microscopy and SEM were used to study degradation behavior of the PARG/BALG film on the surface of NSHGMS.

Figure 5:
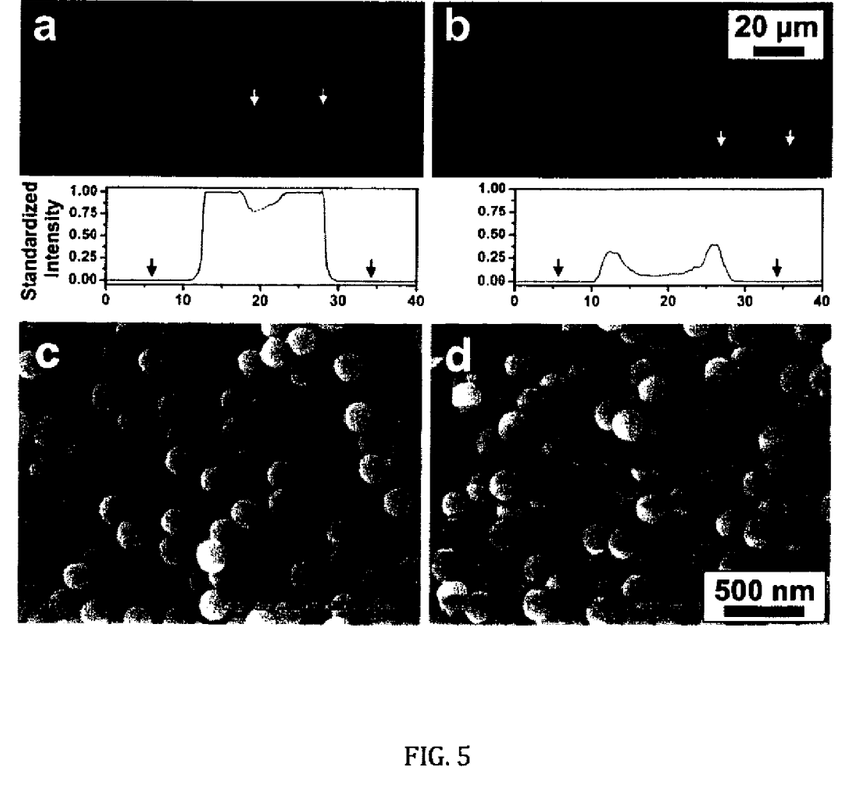
Referring to FIG. 5, fluorescence image and cross-sectional intensity profiles of LbL film on the outmost surface of $^{NS}$HGMS before (a) and after (b) degradation by ALG lyase, together with SEM images of surface morphologies of $^{NS}$HGMS before (c) and after (d) degradation by ALG lyase, are illustrated, in accordance with the embodiments.

As shown in FIGS. 5a and 5b, the degradation process was visualized by conjugating Texas Red labeled Neutravidin on the surface of $^{NS}$HGMS. A strong fluorescence intensity was detected before degradation, indicating that the outermost layer of $^{NS}$HGMS was covered with of the PARG/BALG film. After 10 min incubation with ALG lyase solution, an average 5 times lower fluorescent intensity was observed, suggesting a fast and effective deconstruction of the PARG/BALG film. In addition, SEM images, as shown in FIGS. 5c and 5d, revealed similar surface nanostructures before and after degradation by ALG lyase, and no sign of SiO$_2$ NPs loss was observed. Standard intensity was quantified using ImageJ and the fluorescence intensity of $^{NS}$HGMS before degradation was set to 1.0. The biotin groups on $^{NS}$HGMS surface were tagged with Neutravidin-Texas Red. These two experiments confirmed that the outmost layer of the PARG/BALG film can be rapidly degraded and its degradation does not change the nanotopographical structure on the surface of $^{NS}$HGMS.

Figure 6:
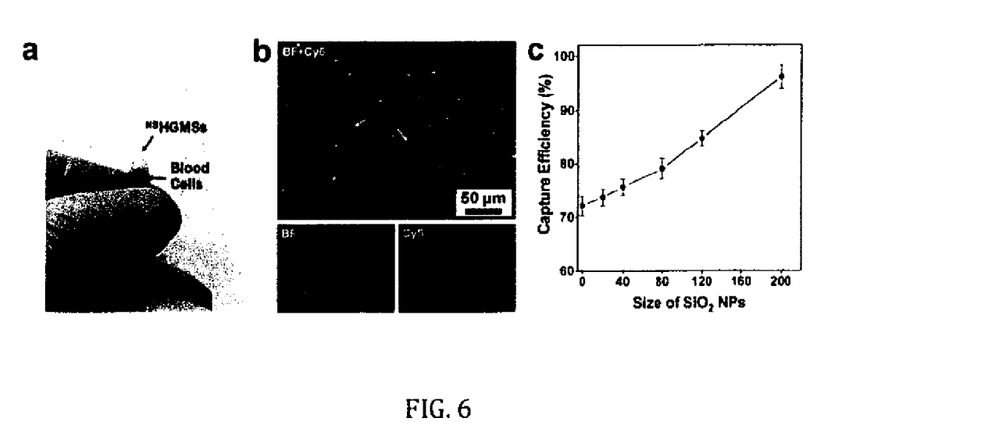
Referring to FIG. 6, illustrated is (a) a digital image of floating $^{NS}$HGMS and separated blood cells in a testing tube, (b) Fluorescence images of captured MCF-7 cells. MCF-7 cells were stained by CellTracker™ Deep Red (presenting in pink), and (c) Capture efficiency of $^{NS}$HGMS covered with $SiO_2$ NPs with different size, in accordance with the embodiments.

To evaluate the cancer cell isolation performance of $^{NS}$HGMS, an EpCAM positive cell line, MCF7 (pre-stained by CellTracker™ Deep Red), was spiked in 5× diluted blood with 1,000 cells/mL was used in the experiment as a model system. The cancer cell spiked blood samples were incubated and rotated with $^{NS}$HGMS in a tube for 1 hour to ensure sufficient contact between cells and $^{NS}$HGMS. Afterwards, the blood samples stood for 5 minutes to allow $^{NS}$HGMS to float to the tip of the collecting tube and the blood cells to settle to the lower half of the collecting tube, as shown in FIG. 6a. $^{NS}$HGMS (with captured cancer cells) were transferred into PDMS microwells, counted under fluorescent microscope, and a typical image is shown in FIG. 6b. Cancer cells were all closely attached to 1-4 $^{NS}$HGMS, and no free-floating cancer cells (i.e. not surrounding by $^{NS}$HGMS) were observed. The capture efficiency of $^{NS}$HGMS covered with SiO$_2$ NPs was compared at different sizes ranging from 20-200 nm. HGMS with smooth surface (no SiO$_2$ NP modification) showed 71.2±2.9% capture efficiency, which is consistent with our previous reported work. By creating nanotopographical structure on the surface of HGMS, cell capture efficiency of 73.7-94.8% was achieved, which also showed an increase trend with the increasing of the size of SiO$_2$ NPs that covered the surface, as shown in FIG. 6c. $^{NS}$HGMS covered with 20 nm SiO$_2$ NPs showing the largest contact surface indicated marginal increment of capture efficiency from 71.2±2.9% to 73.7±1.6%. This result indicated that increasing surface area alone may not be critical in enhancing cell capture efficiency. When $^{NS}$HGMS were covered with 200 nm SiO$_2$ nanoparticles, the capture efficiency was dramatically improved to 94.8±2.2%: this can be attributed to the nanotopographical structures complementary to the filopodium on the cancer cells' surface. Filopodia of cancer cells are finger-like structures that let cells adhere and migrate on external substrates by aligning actin proteins to the points of contact. They are normally 100-300 nm in diameter and 1-3 µm in length. Compared to NsHGMS modified with smaller SiO$_2$ NPs, $^{NS}$HGMS modified with 200 nm SiO$_2$ NPs may form gaps that fit and match the filopodia structure, enhancing shaft and tip adhesion of filopodia, resulting in higher capture efficiency. Similar findings have been reported where higher capture efficiency can be achieved by using a rough surface (150 nm) compared with less rough conditions. Additionally, an improved capture performance was observed by modifying a herringbone-structured microchip with 166 nm polystyrene NPs at a 22% surface coverage.

Figure 7:
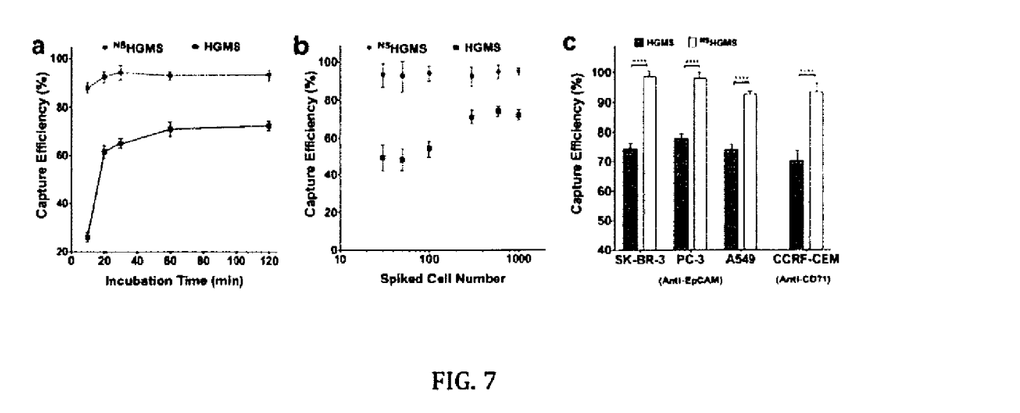
Referring to FIG. 7, illustrated are graphs of (a) capture efficiency of $^{NS}$HGMS and regular HGMS at different incubation times, (b) capture efficiency of $^{NS}$HGMS and regular HGMS with respect to various spiked cell concentrations (cell/mL), and (c) capture efficiency of $^{NS}$HGMS and regular HGMS for different cancer cell lines (1,000 cells/mL), in accordance with the embodiments; and Referring to FIG. 8, illustrated is (a) a graphical illustration of release efficiency and viability of released cancer cells from $^{NS}$HGMS, (b) and imaging of live (green)/Dead (red) staining of captured and released MCF7 cells. MCF7 cells were pre-stained with CellTracker™ Deep Red before spiking into blood (1000 cells/mL), where live MCF7 cells show co-localization of pink and green fluorescent signals, in accordance with the embodiments.

Processing time that allows sufficient cell capture can also be essential to preserve viable CTCs for clinical research. However, although a longer time period can enhance the chance of contact between cells and HGMS, viability of the captured cells may be compromised because a long incubation process could trigger apoptosis of CTCs. To evaluate the minimum time required to isolate high purity cancer cells, we examined capture efficiency at different incubation times, from 10 min to 120 min. As shown in FIG. 7a, maximum capture efficiency around 71.2±2.9% was observed after 60 min for HGMS with a smooth surface; as a comparison, maximum capture efficiency of 92.4±2.3% was observed in 20 min for $^{NS}$HGMS modified with 200 nm SiO$_2$ NPs. This suggests that surface nanostructures of $^{NS}$HGMS could accelerate the adhesion process of cancer cells.

Referring to FIG. 7, illustrated are graphs of (a) capture efficiency of $^{NS}$HGMS and regular HGMS at different incubation times, (b) capture efficiency of $^{NS}$HGMS and regular HGMS with respect to various spiked cell concentrations (cell/mL), and (c) capture efficiency of $^{NS}$HGMS and regular HGMS for different cancer cell lines (1,000 cells/mL). The number of CTCs in blood changes with the stages of cancer, with the detection range from a few to several hundred CTCs per milliliter of blood. Isolation of CTCs using smooth-surface HGMS has dramatically lower efficiency when cancer cell concentration is lower than 1,000 cells/mL. 6 To evaluate the capability of $^{NS}$HGMS on low-cell concentration, we studied isolation of MCF7 with cell numbers ranging from 30 to 1000 cells/mL, comparing them with in same experiments using regular HGMSs. As shown in FIG. 7a, an average 93.6±4.9% of the capture efficiency was obtained for $^{NS}$HGMS in these ranges and decrease of cell concentration did not show significant reduction of capture efficiency. However, regular HGMS showed only 61.3±4.5% of capture efficiency in the same cell concentration range. Specifically, capture efficiency decreased to 47.8±7.6% for a cell concentration of 30 cells/mL. It was shown that invasive cancer cells often contain higher amount of filopodia, which express cell adhesion molecules for cell-cell adhesion, cell-extracellular matrix interaction, and probing of environment Compared with HGMS with smooth surface, the nanostructured surface of $^{NS}$HGMS could fit the finger-like structure of filopodia and enhance both shaft and tip adhesion of filopodia. Adhesion sites formed at the shaft and at the tip are mediated by integrins and are thought to be critical to promote filopodium stability and to regulate filopodia growth. Recent evidence also demonstrated that filopodia shaft adhesions can mature into focal adhesions upon lamellipodia advancement Therefore, nanostructures created by SiO$_2$ NPs could mediate faster adhesion and facilitate stronger binding between cancer cells and $^{NS}$HGMS' surface. Furthermore, during the incubation process, cancer cells may undergo dynamic adhesion/disassociation circles with HGMS, and strong bonding between $^{NS}$HGMS and cancer cells could reduce the disassociation rate of the captured cells. As a result, $^{NS}$HGMS have demonstrated higher capture efficiency, lower detection limit, and shorter processing time.

Next, the application of $^{NS}$HGMS was expanded to isolation of other human cancer cells. Similar experiments on capturing four other cell lines were performed, including A549 (a lung cancer cell line), PC-3 (a prostate cell line), SK-BR-3 (a breast cancer cell line), and CCRF-CEM (a leukemia cell line). Specifically, anti-EpCAM antibody was used to capture A549, PC-3 and SK-BR-3 cells, and anti-CD71 was used to capture CCRF-CEM cells. As shown in FIG. 7c, $^{NS}$HGMS achieved capture efficiencies of 92.7% to 98.5% for all 4 different cell lines. In contrast, only 72.2% to 77.8% capture efficiencies were observed for regular HGMS. These results demonstrate the constant and reliable cell recognition ability of $^{NS}$HGMS.

Figure 8:
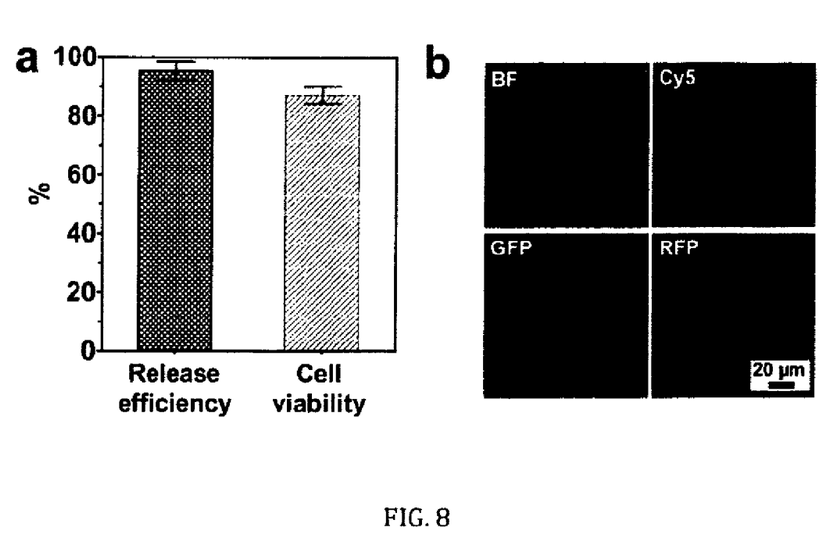

(b) and imaging of live (green)/Dead (red) staining of captured and released MCF7 cells. MCF7 cells were pre-stained with CellTracker™ Deep Red before spiking into blood (1000 cells/mL), where live MCF7 cells show co-localization of pink and green fluorescent signals, in accordance with the embodiments.

Finally, the release efficiency and viability of released cells was investigated. After a 10 minutes of incubation with 1 mg/mL ALG lyase PBS solution, 95.3% of captured MCF7 cells were released from the surface of $^{NS}$HGMS. FIG. 8a illustrates a graphical illustration of release efficiency and viability of released cancer cells from $^{NS}$HGMS. These results were similar to the previously reported work using regular HGMS coated with PARG/BALG film, which suggested that nanotopographical structures on the surface do not affect the degradation behavior of the PARG/BALG film. Furthermore, viability of the released cells was quantified with a standard Live/Dead cell viability assay. FIG. 8a illustrates imaging of live (green)/Dead (red) staining of captured and released MCF7 cells. MCF7 cells were pre-stained with CellTracker™ Deep Red before spiking into blood (1000 cells/mL), where live MCF7 cells show co-localization of pink and green fluorescent signals. As shown in FIG. 8b, the majority of released cancer cells showed vivid green fluorescence. Quantitatively, cell viability was 87.2%, similar to the control cells that did not go through the capture and release process (90.2%). Both released cells and control cells were cultured on a tissue culture plate in a standard condition for an extended period, and no differences in cell adhesion and proliferation were observed between those two groups.

In summary, an LbL assembly method can be applied to tailor surface nanostructure and function of HGMSs for isolation of cells in fluid (e.g., blood or other bodily fluid), including rare cancer cells. Compared to HGMS with smooth surface, HGMS with nanotopographical structures exhibited excellent capture efficiency (93.6±4.9%), rapid processing time (20 min), and low detection limit (30 cells/mL) for commonly used human cancer cell lines. This is attributed to the nanostructure features on the HGMS surfaces and may be complementary to the filopodia on the surface of cancer cells, which mediate faster adhesion and facilitate stronger binding with cancer cells. This highly effective platform for cell isolation does not need specific lab apparatus or any power supplies, and can be combined with other portable diagnosis tools for point-of-care applications in remote and resource-deficient areas. Further, this work expanded the application of the LbL assembly method and provides a simple and effective strategy for creating nanostructures on non-planar substrates.

The invention claimed is:

1. A method comprising:
providing a fluid;
providing hollow glass microspheres in the fluid, the hollow glass microspheres being coated with a biodegradable nanostructured film comprising negatively charged SiO$_2$ nanoparticles and positively charged poly-L-arginine molecules capped with anti-EpCAM antibodies;
dispensing cells in the fluid; and
isolating and recovering cells on the nanostructured film from the fluid using the hollow glass microspheres coated with a biodegradable nanostructured film comprising negatively charged SiO$_2$ nanoparticles and positively charged poly-L-arginine molecules capped with anti-EpCAM antibodies.

2. The method of claim 1, wherein the nanostructured film comprising negatively charged SiO$_2$ nanoparticles and positively charged poly-L-arginine molecules form nanotopographical structures on the surface of the hollow glass microspheres when applied to an external surface of the hollow glass microspheres.

3. The method of claim 2, wherein the negatively charged SiO$_2$ nanoparticles and positively charged poly-L-arginine molecules are applied to the external surface of the hollow glass microspheres using layer-by-layer disposition.

4. The method of claim 2, wherein the external surface of the hollow glass microspheres including the negatively charged SiO$_2$ nanoparticles and positively charged poly-L-arginine molecules is sheathed with an enzymatically degradable LbL film made from biotinylated alginate and poly-L-arginine.

5. The method of claim 4, wherein the negatively charged SiO$_2$ nanoparticles, positively charged poly-L-arginine molecules, and enzymatically degradable LbL film made from biotinylated alginate and poly-L-arginine are applied to the external surface of the hollow glass microspheres using layer-by-layer disposition.

6. The method of claim 4, wherein the negatively charged SiO$_2$ nanoparticles and positively charged poly-L-arginine molecules sheathed with an enzymatically degradable LbL film made from biotinylated alginate and poly-L-arginine is capped with anti-fouling PEG molecules.

7. The method of claim 6, wherein the negatively charged SiO$_2$ nanoparticles, positively charged poly-L-arginine molecules, enzymatically degradable LbL film made from biotinylated alginate and poly-L-arginine, and cap of anti-EpCAM antibodies and anti-fouling PEG molecules are applied to the external surface of the hollow glass microspheres using layer-by-layer disposition.

* * * * *